United States Patent [19]

Lew et al.

[11] Patent Number: 5,599,767
[45] Date of Patent: Feb. 4, 1997

[54] SALT SENSITIVE BINDER SYSTEM

[75] Inventors: Chel W. Lew, San Antonio, Tex.; Keith Branly, Brandon, Fla.; Jesse H. Gaytan, San Antonio, Tex.

[73] Assignee: Micro Flo Company, Mulberry, Fla.

[21] Appl. No.: 250,790

[22] Filed: May 27, 1994

[51] Int. Cl.$^6$ .................................................. A01N 25/26
[52] U.S. Cl. ........................ 504/116; 504/206; 504/244; 504/355; 504/342; 424/405; 424/409; 514/772.2; 71/DIG. 1
[58] Field of Search ...................................... 504/116, 355, 504/244; 71/DIG. 1; 424/405, 409; 514/772.2

[56] References Cited

U.S. PATENT DOCUMENTS

| | | | |
|---|---|---|---|
| 3,565,818 | 2/1971 | Bayless et al. | 252/316 |
| 3,574,133 | 4/1971 | Bayless et al. | 252/316 |
| 3,582,495 | 6/1971 | Emrick et al. | 252/316 |
| 3,629,140 | 12/1971 | Bayless et al. | 252/316 |
| 4,439,488 | 3/1984 | Trimnell et al. | 428/402.24 |
| 4,440,746 | 4/1984 | Maglio | 424/78 |
| 4,777,089 | 10/1988 | Takizawa et al. | 428/402.22 |
| 4,874,611 | 10/1989 | Wilson et al. | 424/410 |
| 4,908,233 | 3/1990 | Takizawa et al. | 427/213.35 |
| 5,064,650 | 11/1991 | Lew et al. | 424/435 |
| 5,160,530 | 11/1992 | Misselbrook et al. | 71/121 |

FOREIGN PATENT DOCUMENTS 380325   1/1990   European Pat. Off. .

OTHER PUBLICATIONS

*ELVANOL,* Du Pont, 3rd ed. (1961).

*Primary Examiner*—José G. Dees
*Assistant Examiner*—Brian G. Bembenick
*Attorney, Agent, or Firm*—Banner & Witcoff, Ltd.

[57] ABSTRACT

Agriculturally effective active ingredients are encapsulated in a "salt sensitive" polymeric binder. Normally, the binder is water soluble and would release the active ingredient when wetted. In the presence of a hardening salt to which the polymer is sensitive, the polymer becomes water insoluble for so long as it is in chemical contact with the hardening salt. This sensitivity is used to control the circumstances and timing of the release of the encapsulated active ingredient.

20 Claims, No Drawings

SALT SENSITIVE BINDER SYSTEM

FIELD OF THE INVENTION

The invention relates to a formulation for delaying the release of an encapsulated agriculturally active ingredient until sufficient moisture is present to activate a release mechanism within the formulation.

BACKGROUND OF THE INVENTION

Although several billion pounds of pesticide are used annually in the United States to control various pests, these pests are still responsible for annual farm production losses equivalent to 30 percent of the total market value of farm products. Part of the problem is due to the lack of full availability of the pesticide to the target area. Environmental conditions such as wind drifting, as well as degradation and evaporation of applied pesticide lead to low efficiency.

Some of the lost efficiency is due to the inherent conflicts between pesticide application and the action mode of the pesticide. For example, many contact pesticides are water soluble and require a certain minimum moisture level before they will move from the soil surface to the subsurface where they can be effective. Other agriculturally effective materials, like water soluble herbicides and fertilizers, must move from the soil or plant foliage surface to the subsurface before they can be effective. The solubility of the material limits the use of area spraying in favor of broadcasting dry solids.

When applied as solids to the soil surface, however, there may be some time delay before sufficient moisture is available to transport the applied materials. This surface exposure is potentially harmful as extended periods of ultraviolet light can significantly degrade many organic chemicals and, since many such chemicals are toxic, nontarget organisms (e.g., birds, rodents, etc.) can inadvertently teed on the applied solids.

Various methods have been used to achieve more efficient pesticide usage. Such methods include protecting the active agent by encapsulated formulations, including controlled release formulations thereof. U.S. Pat. No. 3,565,818 describes a multistep process for encapsulating a core material from a liquid solution containing polyvinyl alcohol and an alkylene glycol cyclic borate ester. As described, the process involves forming the PVA-borate ester liquid phase, adding core material particles to the liquid, and treating the capsules with an aqueous solution of a transition metal salt such as vanadyl sulfate.

U.S. Pat. No. 3,574.133, like the '818 patent, describes a multistep process for producing microcapsules through liquid-liquid phase separation using an aqueous solution of a polyvinyl alcohol and a cyclic borate ester of an alkylene glycol. As described, the process involves forming the PVA-borate ester liquid phase, adding core material particles to the liquid, dehydrating the carrier to encapsulate the core, and optionally treating the capsules with a crosslinking transition metal salt.

U.S. Pat. No. 3,582.495 describes treating polyvinyl alcohol-walled capsules with aqueous vanadium ions. The so-treated capsules are substantially water-insoluble and exhibits a substantial degree or impermeability for materials contained within the capsule walls. In the process disclosed in U.S. Pat. No. 3,629,140, the water solubility of polyvinyl alcohol-walled capsules previously hardened by hydrous vanadyl is re-established by treatment with a material which oxidized the vanadium. The encapsulated material can then be released in water.

U.S. Pat. No. 4,439,488 describes a method of encapsulating chemical biological agents by entrapment within a polyhydroxy polymer borate matrix. In the disclosed process the chemical biological agent is dissolved or dispersed in an aqueous paste of a polyhydroxy polymer. The agent to be encapsulated can be added either prior to or subsequent to pasting of the polyhydroxy polymer. Suitable gel-forming polyhydroxy polymers include natural, derivatized and modified starches, carboxymethylcellulose, dextran, xylan and polyvinyl alcohol. The addition of boric acid or a boric acid derivative, at an alkaline pH, converts the paste into a gel, thereby entrapping the agent in a protective matrix. The gel is then sheared into small particles, alehydrated, sieved and dried to yield a friable granular or powdered material. Rewetting of the product is said to initiate biodegradation of the matrix and release of the active ingredient.

U.S. Pat. No. 4,440,746 describes a slow-release soil pesticide composition. The composition is prepared by dispersing the pesticide in an aqueous solution of polyvinyl alcohol (PVA). An aqueous solution of a borate compound is then added to the PVA-pesticide dispersion and reacted with stirring until a gel is formed. The gel is then treed from water by drying. The dried product is then ground and past through a mesh screen to obtain particles of a desired size. The product is to be applied to soil where it release the pesticide.

U.S. Pat. No. 4,777,089 and U.S. Pat. No. 4,908,233 describe a polyvinyl alcohol-based microcapsule made by adding a substantially water-insoluble core material to an aqueous solution of a polyvinyl alcohol polymer which undergoes phase separation upon the addition of an electrolyte. Addition of the electrolyte causes phase separation whereby the aqueous polymer solution encloses the core material. Suitable electrolytes include salts of inorganic acids such as sulfuric acid, hydrochloric acid, phosphoric acid, boric acid and vanadic acid, and salts of organic acids. Sulfates and phosphates are disclosed as being the preferred salts. Ionic surfactants and amino acids may also be used as the electrolyte. After completion of the phase separation, the capsule wall films are gelled by cooling and then dried to be used as capsules soluble in water. Exemplified core materials include cleaning agents, perfumes and foods. The core component is released by dissolution of the microcapsules when diluted with water during use. In an alternative embodiment, the wall films may be hardened to prepare water-insoluble capsules. Disclosed hardening agents include borax and water-soluble salts of vanadium and uranium. After drying, the capsules are broken to release the core material.

U.S. Pat. No. 5,160,530 describes a process for encapsulating herbicidal compositions (e.g., the yellow polymorphic form of trifluralin with a melt point of 43°–45° C.) by melting or grinding the active ingredient (AI), combining the AI with an aqueous solution containing one of a number of possible film forming polymers, and spray drying the mixture at a temperature within the range from about 500°–220° C.

Japanese patent 74/048073 describes a method for dispersing a hydrophobic substance, such as ink, pigment, perfume, into a solution containing polyvinyl alcohol and then hardening the shell with a hardening agent such as borax.

One might think that a nonaqueous carrier liquid could be used to spray the solids over the treatment area. Unfortunately, nonaqueous dispersion carriers are generally more expensive than water and certainly less readily available. Nonaqueous liquids have also been the subject of a heightened degree of regulatory scrutiny in recent years with the general regulatory preference away from such carriers.

It would be desirable to have an encapsulation formulation for water soluble active ingredients that could be used with an aqueous carrier liquid yet release the encapsulated active ingredient at a target location when sufficient moisture is present to transport the encapsulated active ingredient.

It would also be desirable to have an encapsulation formulation that would permit the addition of additives, including ultraviolet screening agents, to protect UV sensitive active ingredients until moisture is available for dissolution and transport away from the exposed application surface.

SUMMARY OF THE INVENTION

It is an object of the invention to provide an encapsulation formulation useful with water insoluble active ingredients that can permit the encapsulated material to be dispersed in a target location with an aqueous carrier solution yet release the encapsulated active ingredient upon a determinable event.

It is also an object of the invention to permit an encapsulated agriculturally effective, active ingredient to be applied to an area and await the presence of a sufficient level of moisture, without degradation of the active ingredient from causes that include ultraviolet light exposure, to wash the encapsulated material into the soil.

In accordance with these and other objects of the invention that will become apparent from the description herein, a composition according to the invention comprises:

a salt sensitive, polymeric binder that is water soluble except when in chemical contact with a water soluble hardening salt; and an agriculturally effective active ingredient encapsulated within said polymeric binder.

In another aspect of the invention is a process for making the encapsulated solids of the invention which comprises:

mixing (a) an agriculturally effective active ingredient with (b) a salt sensitive, polymeric binder that is water soluble except when in chemical contact with a water soluble hardening salt to form a mixture;

forming particles from said mixture.

In a further aspect of the invention is a process for using the encapsulated solids according to the invention comprises:

distributing in an area to be treated: (a) an agriculturally effective active ingredient encapsulated within an salt sensitive, polymeric binder that is water soluble except when in chemical contact with a water soluble hardening salt; and (b) a water soluble hardening salt in chemical communication with said polymeric binder.

The present invention provides an encapsulation method, product, and application method that are particularly well suited for water insoluble, agriculturally active ingredients. These materials can now be converted into a form that permits application in aqueous media or dry granules with release of the encapsulated material delayed until sufficient moisture is present. The present invention also provides a method for incorporating additives, including ultraviolet light screening agents, to protect the solids until irrigation or rain incorporates the active ingredient into the soil.

DETAILED DESCRIPTION OF THE INVENTION

According to the invention, a "salt sensitive" polymer is used as an encapsulating binder for one or more active ingredients. The polymer is "salt sensitive" in that the polymer is solid and hydrophobic only for so long as a water soluble "hardener" salt is in chemical contact with the polymer. When the hardener salt is removed from contact with the encapsulating binder, the binder becomes water soluble, dissolves, and releases the active ingredient. The process of the invention is particularly advantageous in preparing encapsulated active ingredients containing an agriculturally effective active ingredient whose storage stability is effected by hydrolysis with any moisture in the formulation or which otherwise required a nonaqueous carrier for application by spraying from a tank suspension.

Polymeric, Salt Sensitive Binder

Salt sensitive, otherwise water-soluble polymers suitable for use as the polymeric binders of the invention include film-forming polymers that are water insoluble when in chemical contact with the anion of a water soluble hardening salt and become water soluble when the hardening salt is removed. Preferably, the salt sensitive polymers of the invention exhibit the following properties: (a) the polymers either alone or in combination can be made to dissolve over a period of minutes or days in water at 20° C. in the absence of the hardening salt anion, e.g., a solubility within the range of about 10–80 grams/100 grams of water; (b) the polymer becomes water insoluble when in chemical contact with an aqueous solution having less than 5 weight percent hardening salt; (c) particles made from the polymer are able to stay in suspension for at least 30 minutes and will readily redisperse if agitated; and (d) are chemically inert toward conventional wetting and dispersing aids.

Particularly preferred polymeric binder materials that are sensitive to the presence of a water soluble hardening salt include poly(vinyl alcohol) ("PVA"), acrylic acid-based polymers, and sulfated cellulose. PVA is preferred and inherently affords a measure of ultraviolet light screening to the encapsulated active ingredient.

The physical characteristics of polyvinyl alcohol are, in part, dependent on the degree of polymerization and the degree of alcoholysis, factors which can be controlled during the processing thereof. The term "poly(vinyl alcohol) or PVA", as used herein, should be understood as referring to a polymeric material in which at least 50 percent, by weight, thereof, is composed of vinyl alcohol constituents. The term refers to polymeric materials composed of vinyl alcohol constituents and also to polymeric material containing not only vinyl alcohol constituents but also vinyl acetate, propionate, and/or butyrate constituents providing that the vinyl alcohol constituents make up at least about 50 percent, by weight of the polymeric material.

Any water-soluble grade of polyvinyl alcohol can be used in the practice of the invention. Polyvinyl alcohol useful as a shell for the present invention exhibits a degree of hydrolysis of within the range from about 72 percent to about 99 percent (preferably within the range from about 85 percent to about 89 percent) and a molecular weight within the range from about 2,000 to about 125,000 (preferably within the range from about 3,000 to about 96,000). Commercially available polyvinyl alcohol products within the above are the partially or fully hydrolyzed polyvinyl acetates sold in various molecular weight ranges, such as those available under the trade names GELATOL® (Monsanto) and ELVANOL® (Du Pont).

If desired, one or more additional materials can be added to the encapsulating shell to adjust its properties or characteristics. Undesirable wall brittleness from the polymeric binder can be avoided or mitigated by incorporating therein any of the chemically compatible, known plasticizers. Examples of usable plasticizers include: soluble plant gums (e.g., gum arabic, mono-, di- and polysaccharide sugars), polyhydric alcohols (e.g., mannitol or sorbitol made by reduction of such sugars), alkylene glycols or glycol derivatives, glycerol, or highly polar hydrophilic solvents (e.g., phthalonitrile, acetamide, formamide, dimethyl formamide, and dimethyl sulfoxide). Plasticizers may be incorporated within the polymeric material, during the complex formation between the hardening salt additive, or as a post-contact treatment. A feeding deterrent, e.g., a solid or liquid containing one of the cucurbitacins, can be used to dissuade consumption of the solids by nontarget organisms. Similarly, an emetic can be added to the binder to avoid ingesting a lethal amount of active ingredient.

Other additives to the polymeric binder material include extenders (e.g., starch, dextrin, gelatin, casein and urea), fillers (e.g., diatomites, attapulgites, bentonites, talcs, montimorillonites, perotites, vermiculites, calcium carbonate, corn cob grits and lignin sulfonates), and ultraviolet screening agents (e.g., titanium dioxide, carbon black, activated carbon, and para-aminobenzoic acid). Such additives are preferably added to the product during the encapsulation step and homogeneously mixed therein.

Water Soluble Hardening Salt

Hardening salts used to maintain the polymeric binder in a water insoluble state are generally specific to the polymeric binder. In general, the hardening salts contain a metal or metalloid ion that forms a water insoluble, film-formable complex with the polymeric binder, i.e., the salt precipitates the polymer from solution. Preferably, the hardening salt will precipitate the polymer at a concentration of less than about 5 wt % of the hardening salt based on the total solution weight. Additives to which the preferred polymeric binders is sensitive for solubility is listed in Table 1.

TABLE 1

| Polymer | Water Soluble Hardening Salts |
|---|---|
| polyvinyl alcohol | borates, phosphates, carbonates, hydroxides, and sulfates |
| acrylic acid-based | borates, phosphates, carbonates, hydroxides, sulfates, and alkali metal halogens (e.g., NaCl) |
| sulfated cellulose | borates and sulfates |

Suitable borate salts include the alkali metals (preferably sodium or potassium), alkaline earth metals (preferably magnesium and calcium) and ammonium salts of borate anions such as tetraborate and metaborate anions. Examples include boric acid ($H_3BO_3$) sodium borate (borax), sodium metaborate, and potassium borate.

Boric acid can be used as a source of borate anions when alkaline conditions can be used in the aqueous suspension system containing the borate anions. Under alkaline conditions, boric acid is converted to reactive borate, which then reacts with the polyvinyl alcohol to from the rigid polymeric structure. Suitable boron additives such as TRACITE® (liquid boron 10%), distributed by Setre Chemical Company, are commercially available.

Other water soluble hardening salts for polymers of the invention include disodium phosphate ($Na_2HPO_4$), dipotassium phosphate, sodium sulfate, potassium sulfate, sodium hydroxide, magnesium sulfate, ammonium sulfate, aluminum sulfate and sodium carbonate. Boric acid, disodium phosphate, sodium carbonate and sodium borate are the preferred hardening salt additives for the invention because these materials are nonphytotoxic and, in small quantities, can be beneficial for plant development.

The hardening salt additive is added in an amount sufficient to maintain the polymer in its solid hydrophobic form. The amount required will vary depending on the type and specific amount of binder and fillers used in the particular formulation. Determining a particular amount of hardening salt additive is readily performed by the existing skill level in this art from the description herein. As a guide, sodium borate is used in an amount of less than about 1.5 weight percent, preferably 0.1 to 1.0 percent, based on the weight of the PVA.

Agriculturally Effective Active Ingredients

An agriculturally effective active ingredient (AI), as this term is used herein, refers to any chemical or biological agent used to control pests of any kind or affect the growth of any plant or fungus. Agricultural AIs include fungicities, insecticides, herbicides, plant growth regulators, and essential plant minerals in an amount within the range from about 1 wt % to about 99 wt %, preferably an amount within the range from about 20 wt % to about 90 wt %, and most preferably an amount within the range from about 50–90 wt %. The preferred active ingredients for encapsulation by the present invention are actives that are normally water insoluble, but soluble in alcohol (e.g., methanol or isopropyl alcohol) or aromatic solvents, or which exhibit a solubility in water within the range of 0–40%, preferably within the range of 0–20%. With the present invention, water dispersible encapsulated AI can be prepared at high loading rates without the need for nonaqueous, possibly phytotoxic, solvents to carry the AI from a reservoir tank to a site requiring treatment.

Exemplary fungicities that can be encapsulated according to the invention include: captan; any of the EBDCs (e.g., mancozeb, maneb, niram, metiram, zineb, and ferbam); chlorothalonil; iprodione; ziram: copper salts (e.g., copper sulfate and copper oxychloride); and sulfur.

Insecticides for encapsulation include ethion; ethyl parathion; diazinon; endosulfan; solid and liquid forms of the carbamates (e.g., carbaryl, aldicarb, methomyl, carbofuran, bendiocarb, oxamyl, thiodicarb, trimethylcarb); organophosphates (e.g., phorate, terbufos, fonophos, isofenphos, ethoprop, fenamiphos, disulfoton, malathion, parathion, demeton, dimethoate, chlorpyrifos, diazinon, azinphos-methyl, phosmet, chlorpyrifos-methyl, methyl parathion, diazinon, fonofos, and fensulfothion); compounds which break down an insect's digestive tract tissue including fluorine compounds (cryolite), zinc, and mercury; nicotine; rotenone; neem oil or azadiractin; natural or synthetic pyrethrins; petroleum oils; the halogenated hydrocarbons (e.g., endrin, aldrin and its epoxide, dieldrin, heptachlor, DDT, BHC, lindane, chlordane, methoxychlor, DDD, TDE, and the polychlorinated biphenyls); and microbials (e.g., Bacillus thuringiensis and entomopathic viruses such as the bacculo viruses).

Plant growth regulators useful for encapsulation by the present invention include herbicides and plant growth enhancing amounts of: at least one of the 84 identified gibberillins with GA3, GA4, GAs, GAT and $GA_9$ being the preferred gibberillins for use in the present invention; cytokinins (e.g., zeatin, kinetin, benzyladenine, dihydrozeatin, and isopentenyl adenine); auxins (e.g., indoleacetic acid (IAA), indolebutyric acid (IBA), and naphthalenacetic acid (NAA)); sodium ortho-nitrophenolate; sodium para-nitrophenolate; sodium 5-nitro-guaicolate; polyhydroxycarboxylic acids of 2, 4, 5, and 6 carbon structures; a growth stunting amount of mepiquat chloride; a lethal or sublethal amount of either glyphosate, sulfosate or salts thereof; a growth enhancing amount of bacillus subtilis; trifluralin; paraquat; alachlor; and the phenoxys as well as salts thereof (e.g., 2,4-D).

Essential plant minerals that can be encapsulated according to the invention include any of the minerals known to the art to effect plant growth in conventional amounts. Some examples include boron, nitrates, calcium, potassium, phosphates, iron, magnesium, sulfur, manganese, molybdenum, zinc, and copper.

When agriculturally effective boron compounds are encapsulated as the active ingredient in an salt sensitive polymer that is sensitive to borate anions, like PVA, either a different polymer binder that is not sensitive to the encapsulated material should be used or the core should be coated with an intervening layer to prevent contact between the hardening salt in the core and the salt sensitive polymer binder. Such an intervening layer can be made from a water and alcohol soluble, film-forming layer made from, inter alia, hydroxypropyl cellulose (HPC), polyethylene oxide (PEO), or polyvinyl pyrrolidone (PVP) that will encapsulate the boron and provide a protective layer between the boron AI and the salt sensitive polymer according to the invention. The intervening encapsulation layer prevents contact between the borate AI and the salt sensitive polymer thereby avoiding the permanent formation of an insoluble polymer-borate complex.

As an example of preliminary encapsulation, HPC would first be dissolved in a solvent (alcohol or acetone) and the borate AI added thereto. The solvent is removed to encapsulate the borate AI. The HPC-coated borate is then encapsulated with PVA according to the invention. The PVA-HPC-borate AI encapsulated active ingredient is then dispersed in an aqueous vehicle containing a sufficient amount of the hardening salt to maintain the PVA in a water insoluble state. The water soluble character of both layers permits the encapsulated AI to be released when the hardening salt is removed from the outer layer.

The encapsulate is sufficiently tough to be mechanically handled during manufacture, storage under conventional conditions, packaging, transport and field dispersion. The hardened polymer outer surface is substantially impervious to the active core material, reasonable rugged, and able to mechanically protect the active core material stored therein without detrimental deterioration during storage.

Manufacture

In the encapsulation process, finely divided or liquid AI (in a carrier liquid as a suspension or emulsion or dissolved in a solvent) is first dispersed in or emulsified with either water or an alcohol. This dispersion or emulsion is then formed into discrete, free flowing solid particles by any of the conventional droplet-forming devices, e.g., through rotating nozzles or circular disks exhibiting appropriately sized holes, impacting jets, vibrating membranes, or any other such process that forms droplets having a homogeneous or layered encapsulated active ingredient structure. See, U.S. Pat. Nos. 3,015,128; 3,092,553; 3,310,610; 3,336,155; 3,341,466; and 5,246,636. A rotating circular disk with sized holes along the perimeter thereof is preferred. Other methods include spray drying into a zone heated to a temperature of greater than about 150° C.; spray drying at 20°–110° C. into a collection bed containing starch in an atmosphere of 0–60 % relative humidity with later recovery by screening, spray drying with direct collection and final drying in a fluidized bed, and extrusion into dry granules. The choice between finely divided AI and liquid forms of AI will, in large measure, be dictated by the nature and physical characteristics of the AI to be encapsulated.

In general, finely divided AI solids are preliminarily ground to size with conventional techniques if the AI is not commercially available in a pre-ground form. AI solids exhibiting a size of less than about 100 μm in diameter is well suited for the present invention. The invention is particularly useful for AI solids having a size within the range from about 0.1 μm to about 50 μm and even more useful for AI solids within the range of 2 μm to about 30 μm. As used herein, reference to AI solids includes active ingredients that naturally exhibit a solid form at room temperature, nonaqueous liquids, and liquids that have been previously encapsulated or adsorbed in a solid carrier. Liquid AIs can be used by relying on the agitation in the mixing step to adequately disperse the AI in the salt sensitive, polymeric binder.

The encapsulated active ingredient particles prepared according to the process of the invention generally exhibit a size within the range from about 10 μm to about 3000 μm. Encapsulated products exhibiting a size within the range of about 10–1500 μm, preferably 100–600 μm, for spraying through conventional spraying equipment. Encapsulated solids exhibiting a size within the range of about 600–3000 μm are preferred for use in a dry granular product form.

The amount of water soluble polymer is typically within the range from about 1 to 50 percent, more preferably about 5 to 20 percent, based on the weight of the product. The amount of active ingredient is typically within the range from about 5 percent to about 90 percent and preferably about 50 to about 90 percent by weight of the finished product.

The Methods of Use

Encapsulated AI according to the invention can be applied to plant foliage, soil, animal skin surfaces, and anywhere the AI is needed to be effective. For example, herbicides can be applied to upper or lower plant foliage or to soil for preventing plant growth. Systemic insecticides can be applied to soil, and contact insecticides can be applied to soil or other surfaces where the target insects are known to be travel or feed. The particular situs for treatment and specific application method will depend on the AI and its intended effects.

The encapsulated product particles are distributed or dispersed in the presence of moisture to release the encapsulated AI. The binder will begin to dissolve upon contact with water and release the AI therein. As such, the encapsulated AI can be applied by a variety of methods and forms including dry granules, an aerosol, or sprayed from an aqueous carrier. When applied as a granule, the hardening salt is coated either onto the granule with a water soluble carrier or salt or onto the individual encapsulated AI solids before forming the granule. Any of the conventional granule formation methods can be used. In general, granulation is performed by spraying an AI in liquid or finely divided solid form onto a ground carrier. Other granulation processes include low pressure extrusion in a binder, briquetting, and pelletizing.

When used as an aerosol, the encapsulated active ingredient dispersed in an aqueous solution with the hardening salt and a propulsion agent are sealed in a pressurized container. Any of the conventional propulsion agents can be used, e.g., fluorocarbons, chlorofluorocarbon gases, C1–C4 alkane gases, dimethyl ether, and vinyl chloride monomer.

The encapsulated AI is preferably mixed with cool water in a spray tank. As is conventional, spray tanks contain cool water and one or more adjuvants, surfactants, or other co-applied material. Distribution from the tank is through conventional spray nozzles.

The encapsulated AI is preferably suspended in a spray tank containing an aqueous solution with an amount of hardening salt that is sufficient to maintain the polymer in a water-insoluble state. This method is preferred for distributing the encapsulated AI solids over large agricultural fields or forests using airplanes, boom sprayers, or any such spray application equipment before and/or after planting. Upon distributing the solids from the tank, a small quantity of the hardening salt adheres to the outer surface of the encapsulated AI, maintaining the insoluble character of the polymer and preventing premature release of the active ingredient.

Allowing the solids to be washed with irrigation, rain, or dew water removes the hardening salt from contact with the encapsulating polymer and permits release of the active ingredient. A slow, extended release of the encapsulated active ingredient will occur with the inherent moisture found in most soils. Fields and gardens in which pesticides, attractants, repellents, plant growth regulators and fertilizers are normally used contain sufficient levels of natural or irrigation moisture that is sufficient to wash away the hardening salt and initiate dissolution of the polymeric binder with the attendant release of the active ingredient within. By avoiding nonaqueous carrier liquids with the encapsulation formulation of the invention, the invention provides for reduced environmental exposure to nonaqueous solvents, reduces the carrier liquid cost for applying the encapsulated active ingredients, reduces phytotoxicity to treated plants, reduces the exposure concerns when handling the encapsulated active ingredients, and extends their effective life in proportion to the amount of environmental moisture.

In the preferred embodiment, the active ingredient is $\alpha,\alpha,\alpha$-trifluoro-2,6-dinitro-N,N,-di-n-propyl-p-toluidine (trifluralin) in an amount within the range of about 65–90 wt %, and the salt sensitive polymer is poly(vinyl alcohol) with the associated "additives" being either boric acid or disodium phosphate. This product is particularly useful in preemergent weed control because the amount of hardening salt adhering to the dispersed product is proportional to the concentration in the spray tank and can be adjusted to correspond to the minimum amount of water required for weeds to germinate in a particular geographical area. By increasing the amount of boron salt in the tank, the minimum precipitation level for release can be raised. Insufficient moisture for germination will also be insufficient to release the trifluralin. Additionally, the boron salt is a beneficial mineral for plants.

Due to degradation from UV light, the use of trifluralin has required the relatively expensive step of incorporating the AI into the soil shortly after application. With the present invention, however, trifluralin can now be used in the more convenient and less costly surface application methods for pre-emergent weed control. Incorporation into the soil will occur from the effects of rain on encapsulated trifluralin applied to the soil surface.

A combination of regular soluble granulated herbicides and encapsulated active ingredients with a delayed release mechanism according to the invention can be applied in combination. A combination of encapsulated active ingredients having varying amounts of additives incorporated therein is also contemplated for use. One such example is a combination of herbicide that releases immediately in combination with another having a polymeric shell that dissolves more slowly. The immediately released herbicide provides immediate control while the extended release herbicide is available for continued control after the release conditions are met.

EXAMPLES

The following examples are for purposes of illustration only and are not intended to limit the scope of the invention. In each example, finely divided trifluralin (<50 μm) was added to a solution containing PVA and sorbitol, mixed in a high shear mixer until homogeneous, formed into solids by spraying droplets of the mixture either into a drying zone heated to a temperature of at least 150° C. and allowing the droplets to solidify into free flowing solids as they pass through the heated zone (ex. 1) or spraying droplets of mixture into a starch bed and allowing the droplets to form free flowing solids therein at ambient conditions that included 50 % relative humidity and a temperature of 20°–25° C. (ex.

Example 1

Trifluralin was encapsulated with poly(vinyl alcohol) and the additives listed in Table 2. The particle size range was generally within the range of 53–106 μm with an average particle size of about 75 μm.

TABLE 2

| Ingredient | Weight Percent |
|---|---|
| Poly(vinyl alcohol) (Mowiol ™ PVA 3-83) | 15 |
| Sorbitol | 3 |
| Titanium dioxide | 2 |
| Trifluralin (96% purity) | 80 |

The encapsulated trifluralin particles suspended well into an aqueous solution containing only boric acid or sodium borate as the hardening salt for the PVA.

Example 2

Trifluralin was encapsulated with poly(vinyl alcohol) and a solvent for the trifluralin to assist spreading and particle size reduction during the mixing process. The formula is shown in Table 3.

TABLE 3

| Ingredient | Weight Percent |
|---|---|
| Poly(vinyl alcohol) (Mowiol ™ PVA 3-83) | 15 |
| Sorbitol | 3 |
| Titanium dioxide | 2 |
| Trifluralin (96% purity) | 72 |
| Isopropyl myristate | 8 |

Free flowing particles were recovered from the starch bed by waiting for the solids to dry to less than about 15 wt % moisture and passing the starch through a screen with openings of less than 44 μm. Encapsulated trifluralin was recovered, and the starch was ready for reuse. The particle size range of the product was generally within the range of 53–106 μm with an average size of about 75 μm. The product dispersed easily in an aqueous solution containing only either boric acid or sodium borate as the hardening salt for the PVA.

We claim:

1. A sprayable aqueous composition comprising:
   discrete, free flowing solid particles comprising a salt sensitive, polymeric binder that is water soluble except when in chemical contact with a water soluble hardening salt and an agriculturally effective active ingredient encapsulated within said polymeric binder; and an aqueous carrier medium containing said water soluble hardening salt in an amount sufficient to maintain said polymer in a solid, hydrophobic form.

2. The composition of claim 1 wherein said polymeric binder comprises a polymer that becomes water insoluble in chemical contact with an aqueous solution containing less than 5 weight percent of a water soluble salt selected from the group consisting of borates, phosphates, carbonates, and sulfates.

3. The composition of claim 2 wherein said polymeric binder comprises a polymer that becomes water insoluble in chemical contact with an aqueous solution containing boric acid, sodium borate, or disodium phosphate.

4. The composition of claim 1 wherein said polymeric binder comprises poly(vinyl alcohol) or sulfated cellulose.

5. The composition of claim 1 wherein said active ingredient is a fungicide, insecticide, plant growth regulator, or essential plant mineral.

6. The composition of claim 5 containing 20–90 wt % of a plant growth regulating agent.

7. The composition of claim 6 wherein said plant growth regulating agent is selected from the group consisting of trifluralin, paraquat, glyphosate and salts thereof, and alachlor.

8. The composition of claim 7 wherein said plant growth regulating agent is trifluralin.

9. The composition of claim 7 wherein said plant growth regulating agent is paraquat.

10. The composition of claim 1 further comprising a plasticizer.

11. The composition of claim 1 further comprising an ultraviolet screening agent.

12. A process for making encapsulated active ingredients, said process comprising the steps:

mixing (a) an agriculturally effective active ingredient with (b) a salt sensitive, polymeric binder that is water soluble except when in chemical contact with a water soluble hardening salt to form a mixture;

forming discrete, free flowing solid particles containing said active ingredient and said polymeric binder; and dispersing said particles in a spray tank containing water and said water soluble hardening salt in an amount sufficient to maintain said polymer in a solid, hydrophobic form.

13. A process according to claim 12 wherein the forming step comprises:

spraying droplets of said mixture into a zone heated to a temperature of at least 150° C. and allowing said droplets to form free flowing particles as they pass through said zone.

14. A process according to claim 12 wherein the forming step comprises:

forming particles from said mixture by spraying droplets of said mixture into a starch bed and allowing said droplets to form free flowing solids.

15. A method for applying an agriculturally effective active ingredient, said method comprising the steps:

distributing in an area to be treated an aqueous composition comprising: (a) discrete, free flowing solid particles comprising an agriculturally effective active ingredient encapsulated within an salt sensitive, polymeric binder that is water soluble except when in chemical contact with a water soluble hardening salt; and (b) a water soluble hardening salt whereby a quantity of said hardening salt adheres to the outer surface of the polymeric binder and maintains said polymer in a solid, hydrophobic form until said salt is removed.

16. A method as in claim 15 wherein the distributing step comprises:

distributing in an area to be treated: (a) solids containing an agriculturally effective active ingredient selected from the group consisting of fungicides, insecticides, plant growth regulators, or essential plant minerals encapsulated within an salt sensitive, polymeric binder selected from the group consisting of poly(vinyl alcohol) and sulfated cellulose that is water soluble except when in chemical contact with a water soluble hardening salt; and (b) a water soluble hardening salt selected from the group consisting of borates, phosphates, carbonates, and sulfates in chemical communication with said polymeric binder.

17. A method as in claim 16 wherein the distributing step further comprises:

introducing solids containing an agriculturally effective active ingredient encapsulated in an salt sensitive, polymeric binder into an aqueous solution containing a water soluble hardening salt which causes said polymeric binder to become water insoluble when in chemical contact with said salt; and distributing said solids onto an area or surface to be treated with said active ingredient.

18. A method as in claim 17 further comprising:

distributing said solids onto plant foliage.

19. A method as in claim 17 further comprising:

distributing said solids onto soil.

20. A method as in claim 19 comprising:

introducing solids containing trifluralin encapsulated in a polymeric binder comprising poly(vinyl alcohol) into an aqueous solution containing a water soluble hardening salt which causes said polymeric binder to become water insoluble when in chemical contact with said salt; and spraying said solids and said solution onto soil in a quantity sufficient to affect the growth of weeds.

* * * * *